(12) United States Patent
Blattner

(10) Patent No.: US 11,142,745 B2
(45) Date of Patent: *Oct. 12, 2021

(54) MATERIALS AND METHODS FOR EXTENDED CONTINUOUS FLOW FERMENTATION OF REDUCED GENOME BACTERIA

(71) Applicant: Scarab Genomics, LLC, Madison, WI (US)

(72) Inventor: Frederick R. Blattner, Madison, WI (US)

(73) Assignee: SCARAB GENOMICS, LLC, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/824,583

(22) Filed: Mar. 19, 2020

(65) Prior Publication Data

US 2020/0216798 A1 Jul. 9, 2020

Related U.S. Application Data

(63) Continuation of application No. 15/563,540, filed as application No. PCT/US2016/025588 on Apr. 1, 2016, now Pat. No. 10,604,736.

(60) Provisional application No. 62/142,282, filed on Apr. 2, 2015.

(51) Int. Cl.

| C12N 1/20 | (2006.01) |
|---|---|
| C12M 1/00 | (2006.01) |
| C07K 14/21 | (2006.01) |
| C07K 14/34 | (2006.01) |
| C07K 14/47 | (2006.01) |
| C12M 1/02 | (2006.01) |
| C12P 21/00 | (2006.01) |

(52) U.S. Cl.
CPC ............ *C12N 1/20* (2013.01); *C07K 14/21* (2013.01); *C07K 14/34* (2013.01); *C07K 14/47* (2013.01); *C12M 23/58* (2013.01); *C12M 27/00* (2013.01); *C12M 29/00* (2013.01); *C12M 29/06* (2013.01); *C12P 21/00* (2013.01)

(58) Field of Classification Search
CPC ........ C07K 14/34; C07K 14/21; C07K 14/47; C07K 14/245; C07K 14/285; C07K 2319/02; C12N 1/20; C12N 15/74; C12N 15/70; C12N 9/1022; C12N 9/1048; C12N 1/08; C12N 15/52; C12N 9/1205; C12N 9/18; C12N 1/205; A61K 2039/505; A61K 2039/52; A61K 2039/585; A61K 35/74; A61K 39/0011; A61K 39/02; A61K 39/39558; C12M 23/58; C12M 29/00; C12M 29/06; C12M 27/00; C12P 21/00; C12P 19/02; C12P 21/06; C12P 7/18; C12P 7/22; C12R 1/19; C12R 2001/19; C12Y 202/01006; C12Y 204/00; C12Y 207/01011

See application file for complete search history.

(56) References Cited

U.S. PATENT DOCUMENTS

| 2006/0199260 A1 | 9/2006 | Zhang et al. |
|---|---|---|
| 2008/0318283 A1 | 12/2008 | Carnes |
| 2011/0008831 A1 | 1/2011 | Emmerling et al. |
| 2013/0330768 A1 | 12/2013 | Stahn |
| 2017/0073379 A1* | 3/2017 | Blattner ............... C07K 14/34 |

FOREIGN PATENT DOCUMENTS

| CN | 1215083 A | 4/1999 |
|---|---|---|
| CN | 201707311 U | 1/2011 |
| CN | 103298925 A | 9/2013 |
| CN | 203807468 U | 9/2014 |
| JP | S 54-070492 A | 6/1979 |
| JP | S 63-503112 A | 11/1988 |
| JP | 2008-113600 A | 5/2008 |
| JP | 2014-500032 A | 1/2014 |
| WO | 1987/003909 A1 | 7/1987 |
| WO | 2005/087940 A1 | 9/2005 |
| WO | 2012/085162 A1 | 6/2012 |
| WO | 2013/059595 A1 | 4/2013 |
| WO | 2014/146933 A1 | 9/2014 |
| WO | 2015/073720 A1 | 5/2015 |

OTHER PUBLICATIONS

Notice of Allowance for Japanese Patent Application No. 2017-551100 dated Jun. 26, 2020 and allowed claims.
Notice of Reasons for Rejection of Japanese Patent Application No. 2017-551100 dated Dec. 13, 2019 from the Japanese Patent Office (with an English translation).
Decision to Grant a Patent for Japanese Patent Application No. 2017-551100 dated Jun. 26, 2020 and allowed claims.
Posfai, G., et al., P17. Reduced Genome *Escherichia coli*: A Platform for Genomic and Metabolic Engineering, EC-US Task Force on Biotechnology Research, Workshop on Metabolomics and Environmental Biotechnology, p. 44 (Jun. 2008).
International Search Report of PCT/US2016/025588 dated Jun. 23, 2016.
Written Opinion of PCT/US2016/025588 dated Jun. 23, 2016.

* cited by examiner

*Primary Examiner* — Deborah K Ware
(74) *Attorney, Agent, or Firm* — Much Shelist, PC; Christopher M. Cabral

(57) ABSTRACT

Methods and compositions for long term continuous flow fermentation using a two vessel continuous culture fermentation apparatus are described.

8 Claims, 13 Drawing Sheets

MATERIALS AND METHODS FOR EXTENDED CONTINUOUS FLOW FERMENTATION OF REDUCED GENOME BACTERIA

CROSS-REFERENCE TO RELATED APPLICATIONS

This application is a continuation of U.S. application Ser. No. 15/563,540, filed Sep. 29, 2017, which is a 35 U.S.C. 371 national stage application of International Application Number PCT/US2016/025588, filed Apr. 1, 2016, which claims the benefit of U.S. Provisional Application No. 62/142,282 filed Apr. 2, 2015, the entire contents of each of which are incorporated herein by reference.

FIELD OF THE INVENTION

A two-vessel continuous flow system in conjunction with low mutation reduced genome bacterial strains provides a platform for long term extended fermentations. Such systems require modification of standard fermentation devices such as probes, pumps and monitoring systems as well as improved procedures for feed delivery, culture monitoring and product harvesting methods. An optimized two-vessel system for producing large quantities of fermentation products from small volume, long duration continuous fermentations represents a significant improvement over existing fermentation strategies.

BACKGROUND OF THE INVENTION

Bacterial fermentation is the most efficient industrial process for manufacturing biological molecules, and has been the method of choice for bio-therapeutics production. In the past few years, however, drug manufacturers have begun to face up to the problems associated with batch and fed-batch fermentation, in which the whole process takes place in a single vessel over a period of a week or more yielding only one fermentation vessel volume of fermentate. Cells are grown to relatively high density (~OD=100) and then induced to make the product for a relatively short period (hours) before they start to die. Batch processes are vulnerable to failure, many due to genetic instability of the bacterial strains used, which are often metabolically inefficient and highly subject to stress under induction. Metabolic stress can induce responses in the cells which can compromise product formation and integrity and damage the genome, slow growth or even kill cells. Mutants that no longer make product can quickly overtake the culture or bacteriophage or lysogens from the genome can kill or lyse the entire culture.

A more efficient and reliable fermentation protocol is a process where nutrients are continuously added to the culture as needed and bacteria and products are harvested continuously. Such continuous flow bioreactor systems may be operated as a chemostat, in which the volume of the bioreactor is held constant by synchronizing the input of nutrient medium to the outflow of cells and spent media (the dilution rate) to produce a physiological steady state in the resident bacteria. In commercial application this steady state is ideally set to hold the bacterial cells at the physiological optimum point of maximum product formation. Unfortunately, chemostat operations are highly sensitive to mechanical disruption since the delicate balance established by the dilution rate can be upset by physical changes to flow through the system. Furthermore, genetic changes in the population within the bioreactor can also upset the physiologic steady state or nonproductive mutants can take over the culture [See van Heerdon and Nicol, Microbial Cell Factories 12:80 (2013)].

In addition to the mechanical and genetic challenges inherent in continuous flow bioreactor operations, there are difficulties associated with establishing a steady state in traditional single vessel chemostats with recombinant systems requiring induction of gene expression to produce the product of interest. Typically, such a system is grown in an initial batch or fed batch phase to a predetermined optimal cell density and then exogenous inducer such as IPTG is added and the chemostat mode then established using a feed input containing properly diluted inducer to maintain the level of induction throughout the course of the fermentation. Not only is this technically difficult, but frequently, bacteria that undergo mutational changes that lessen the burden of induced gene expression tend to overgrow the population within the bioreactor resulting in a loss of productivity. Such problems also occur in batch fermentations, however the impact on productivity is generally less significant since the batch or fed batch fermentation has a finite (and generally short) lifetime.

More recently, a continuous flow fermentation system was described in which two-vessels were combined in a process to produce covalently closed circular DNA plasmids by induction of a temperature sensitive origin of replication (U.S. Patent Publication No. 2008/0318283). In this process the cells in the first vessel were grown at a relatively low temperature resulting in low plasmid copy number within the cells. Under this condition the desired cells containing the highly inducible plasmid and undesired cells comprising mutations that decrease overall plasmid copy number have little or no growth advantage between themselves. In this system only upon passage into the higher temperature second vessel is plasmid copy number induced and a selective advantage conferred upon the undesired cells containing plasmids with lower induced copy number. Thus, the first (seed) vessel serves as a continuous inoculum for the second (production) vessel. Continuous inoculation with the desired cells limits the ability of undesired faster growing mutants becoming established in the production system, since the mutants are subject not only to continuous washout, but to continuous replacement by uncontaminated inoculum.

Although this presents an elegant solution to part of the problem of production cell stability it is only a partial solution. Direct cellular engineering to improve production strain stability can be coupled with the two-vessel system to improve the overall process. Further, it is not entirely certain that induction schemes involving chemical or biological induction, rather than thermal induction, will prove equally useful and they will, of necessity require more complex input streams to provide a continuous level of inducer within the production vessel while keeping the seed vessel free from inducer. In addition, a two-vessel system may provide an ideal framework for determining optimum production conditions by allowing serial variation of different conditions with a uniform cell source. In this case, the production vessel is held at the desired condition for the required period of time to establish the steady state, samples are taken for productivity determination and the next experimental condition established merely by modifying the feed or other experimental parameter (oxygen tension, pH, amount of inducer, etc.) and allowing the system to come to the new steady state before taking a new round of samples. Such a process can be repeated any number of times without requiring any input from the user other than providing the new experimental inputs. Much of this can be done entirely by preprogrammed computer controllers. Further, a single seed vessel can serve multiple production vessels facilitating parallel experimental or production operations.

Using an appropriate apparatus, referred to here as the "C-flow" apparatus and specially engineered bacteria, continuous processes use less energy, manpower, downtime, capital equipment outlay and footprint, and when set up correctly can run for months, producing on the order of a vessel volume of fermentate per day, at cell densities and product concentrations more than double that of a fed batch process for the same product. With the C-flow system a vessel of a given size can produce from 5 to 50 times more product than a comparably sized vessel using a fed batch system within a period as short as three weeks.

SUMMARY OF THE INVENTION

In one embodiment the device employs a pair of 2 L fermentation vessels, for example, from a DASGIP-Pro laboratory fermenter as diagrammed in FIG. 1. Each vessel was configured as an independent continuous flow chemostat, regulated as indicated with standard DASGIP accessories. Each chemostat is fed glucose minimal salts medium using a dual feed approach that separates delivery of phosphate from the other media components to avoid precipitation and discoloration. The two feed bottles required for each chemostat each rest on a single Mettler balance which gravimetrically controls peristaltic pumps with matched delivery tubes via a set of programmable controllers.

The first, "seed" chemostat produces a continuous supply of uninduced recombinant E. coli containing an expression vector encoding the desired product. The second, production chemostat is fed with media containing IPTG inducer. The two tanks are connected in series by a transfer pump drawing from a spill tube to maintain the upstream tank's fluid level. The seed tank feeds into the production tank and the production tank is pumped into a refrigerated collection vessel with a sample portion being diverted through a de-bubbler to a refrigerated fraction collector for assay.

In another embodiment, the production organism is a multiple deletion strain (MDS) E. coli which has been genetically engineered for high metabolic efficiency, the ability to grow on glucose minimal salts medium and a 100 fold lower mutation rate than wild type E coli. In some embodiments, the production strain is MDS69 meta ΔrecA. For periplasmic production a signal peptide is used to facilitate transport of the protein product into the periplasm of the production organism.

To achieve the C-flow system shown in FIG. 1, the following modifications to the standard DASGIP Pro system were made to integrate control of the balances into the controller software to allow accurate gravimetrically regulated feeding, separate the feed streams to avoid precipitation; reformulate high concentrated media stocks in two separate reservoirs on a single balance in order to integrate control of the two feed streams via a single control channel. Since stock DASGIP feed pumps are not sufficiently powerful, external feed pumps were used instead, thus requiring two feed lines and two pumps per vessel. Even with a single feed stock the DASGIP pumps lack the flow rate capacity for the end of the exponential fed batch phase. The external feed pumps are controlled by DASGIP software via analog signal. The original DASGIP feed pumps are used for anti-foam delivery as well as pH control and nitrogen feed by ammonium hydroxide addition. Off-gas exhaust was re-plumbed into a sterilizable catch vessel to capture any foam over. An extra pump is required to transfer culture from seed vessel to production vessel and from the production vessel to down-stream-processing. The gassing sparger was modified to allow for runtime clearing by a solenoid activated push rod periodically thrust through the gas outlet end of the sparger tube to remove any accumulated obstructions. Extra dip tubes were also required for additional monitoring and sampling. A de-bubbler is used to split the product stream into a large product pool and a fraction collector for small hourly samples to monitor the yield profile and other parameters over time In another embodiment, shown in FIG. 2, the system incorporates a unique flow cell capable of stably reading very high ODs from very small volumes of sample presented via a circulation loop, or in another embodiment, drawn from the fraction collector stream and discarded after measurement. In typical fermentations samples must be diluted and background absorbance or light scattering must be measured against a standard and the device set to provide the necessary compensation prior to measuring samples. This process is not useful for monitoring fermentations for long periods of time during which the background compensation is likely to drift significantly and readjustment would require breaking the closed fluid circuit thus jeopardizing system sterility. Moreover the high cell concentration of C-flow fermentations (>200 OD) as well as the relatively low ODs encountered in the setup phase are difficult to directly measure in an entirely "hands-off" automated system. FIG. 2 illustrates the inventive solution to this problem. In the illustrated embodiment we combine an automated continuous flow diluter with a very short path flow cell with a path length of 1 to 2 mm and a stable, sensitive optical density reader comprising two photodiode detectors one of which reads the output of a single LED source directly while the other detector reads through the sample stream passing through the flow cell. In an embodiment the two photodiodes are comprised of different materials, one sensitive to light wavelengths of 500 to 600 nm, which are typically used to measure cell numbers by refraction, and the other sensitive too much longer wavelengths, 890 to 1200 nm, that are progressively less sensitive to the presence of cell sized particles in solution. Variations of light emitted by the LED source over time can be continuously adjusted by adjusting the dilution rate from 1:100 shown in FIG. 2, using a shorter or longer path length, or switching in photodiode pairs of different light scattering sensitivity (FIG. 2).

In another embodiment the C-flow system is inoculated with a reduced genome bacterial strain genetically engineered to remove all transposable genetic elements, to enhance genetic stability, to improve metabolic capacity and to allow production of a desired product such as a recombinant protein, nucleic acid or small molecule. The reduced genome bacteria may contain one or more plasmids or other episomal or genomic constructs to facilitate production of such recombinant proteins, nucleic acids or small molecules. The reduced genome bacterial strain may possess modifications to enhance genetic stability such as those described in U.S. Pat. Nos. 9,085,765, 8,178,339, 8,043,842 and 6,989,265 and International Publication No. WO/2013/059595 and may also possess modifications to improve metabolic capacity such as those described in International Publication No. WO/2015/073720, the contents of each of which are incorporated herein by reference in their entirety.

DESCRIPTION OF THE DRAWINGS

FIGS. 4 A-C depict schema for multi gravimetric feed systems to provide multiple feed inputs to facilitate separate feed components to enable design of experiments (DOE) to fine tune the balance of such components for optimizing metabolic state, nutrient input and product quality.

DETAILED DESCRIPTION OF THE INVENTION

Figure 1:
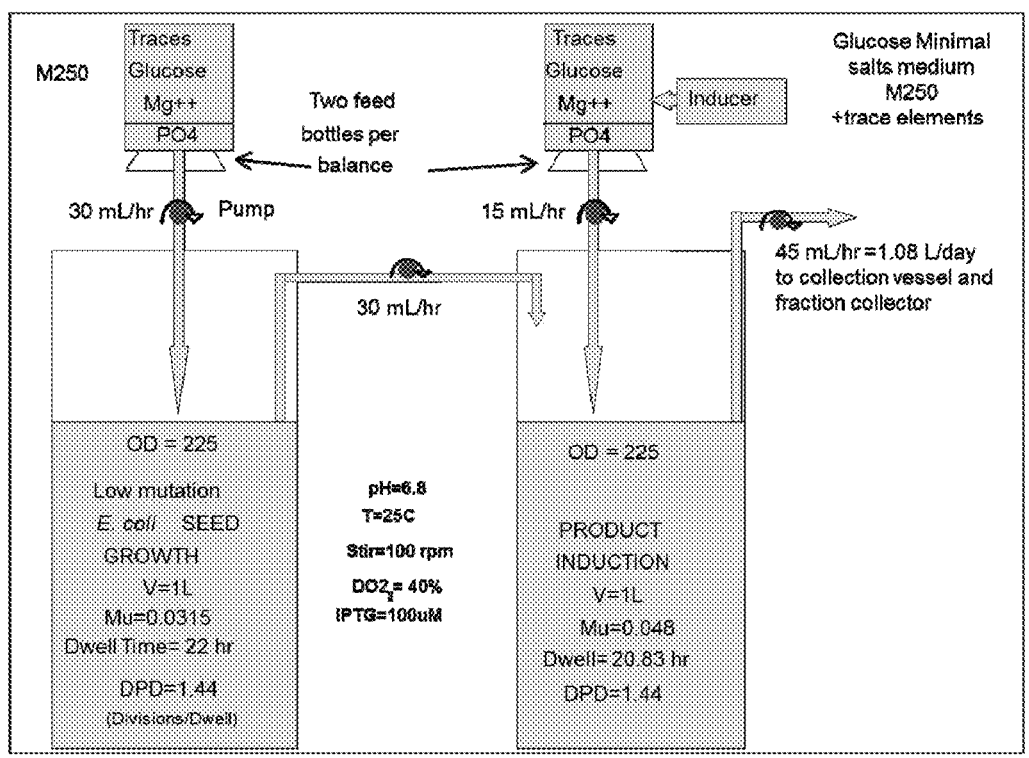
FIG. 1 represents a schematic of the C-flow apparatus.
Figure 2:
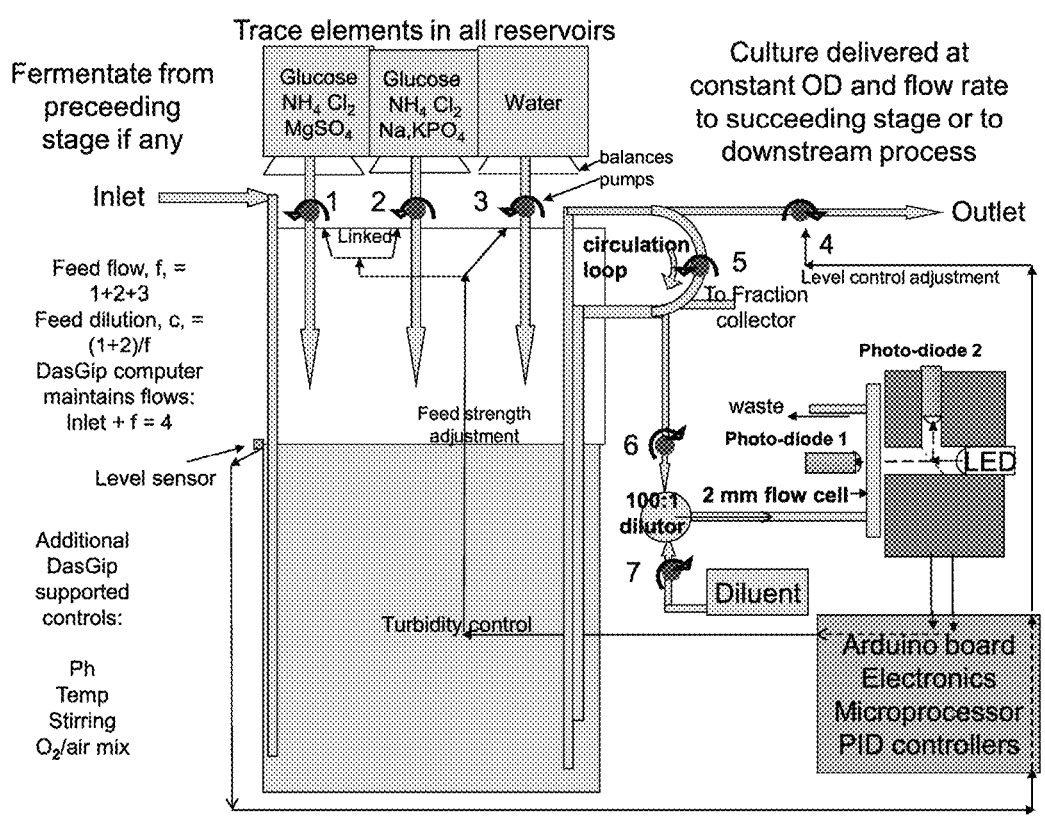
FIG. 2 is a schematic of the C-flow apparatus showing details of 1-2 mm flow cell device for monitoring cell concentration in fermentation vessels.

The present invention comprises a system for producing large quantities of biological products from a production organism cultured in a two-vessel continuous flow fermentation in which one vessel operates to provide the other vessel a continuous stable source of uninduced production cells. Such a system, when coupled with genetically stabilized production cell strain and certain fermentation hardware modifications provides a stable production platform as well as a versatile system for rapid and reproducible experimental determination of optimal production conditions.

The robustness and convenience of the C-flow system are remarkable. Fermentation vessels were initially filled with parallel fed batch fermentations which were grown with no inducer and with the transfer pumps between the vessels switched off. After the fed batch phase of growth was complete a constant feed rate of 30 ml/hour was established for each vessel and the transfer pumps turned on. Within 24 hours the target OD had been reached in each tank and the feed into the production tank was reduced to 15 ml/hr. the inducer feed was started and production of product monitored. After product output had stabilized optimization experiments were performed. Over the period of a month 13 different fermentation conditions were tested in a single continuous fermentation and the actual effort required was minimal. Operations were observed from time to time via a VPN connection to the control computer and via a "nannycam" to check for visible problems. Each morning proper operation was monitored and after 2 or 3 dwell volumes at one condition, the system was transitioned to the next condition. In one series of experiments the highest production rate for a test protein yielded a continuous flow of completely soluble protein of 72 g/month from fermentate at an OD600 over 200 and a flow rate of 1 L/day. Bearing in mind that most organizations are hard pressed to complete fed batch fermentations at a rate of one per week, the expected yield of these two fermenter vessels, if they were operated as two independent fed batch fermentations each running once per week, would be 4 weeks * 2 vessels * 1 L/vessel * 1.2 g/L of product=9.6 grams of product, a factor of 7.5 less efficient use of the equipment than the C-flow configuration. In addition, the eight corresponding fed batch fermentations would be far more costly, labor intensive and prone to variation in performance than the single C-flow fermentation.

Several other observations are pertinent. Occasional operational disruptions occurred, for example, as result of clogged tubing, feed bottles running out, the oxygen supply interrupted or the culture over-induced. The ability of the C-flow system to recover quickly is remarkable. In fed-batch fermentation an anaerobic interlude or any event that slows cell growth rapidly produces a significant accumulation of glucose resulting in a physiologic runaway feedback loop that is difficult or impossible to recover from. In the C-flow system this does not happen because the rates of glucose being fed to maintain the bioreactor at high density are so much lower than those required to generate such a crisis, so the runaway feedback loop does not easily happen. Acetate may be formed, but unless anaerobic conditions persist for several hours, the acetate is re-assimilated or flushed out before it can reach highly toxic levels.

The following calculation, based on data collected from a periplasmic test protein, provides a conservative estimate of the protein made in the C-flow fermenter. Fed batch fermentations of this test protein take a week to complete, and yield fermentate at a rate of about 6 L/168 hr, which is equivalent to about 0.03 L/hr and a product yield of 1 g/L, producing a total of 5.04 g of test protein. The 1 L laboratory prototype C-flow system can also produce test protein at 1 g/L at a rate of 2.4 L/day (0.1 L/hr) using a working volume of 1 L. In the same time, then, the C-flow system delivers 16.8 g of test protein, 3 times the amount of test protein from ⅙ the working volume, or about 18 times more effectively.

Therefore, if a 6 L C-flow system, which requires a 12.5 L vessel and is the largest size that could conveniently fit into a standard containment hood, were to be run continuously for a year it could produce 3000 L of fermentate at an $OD_{600}$ of 250. This would match the performance of a 3000 L working volume fermenter run once, or a 120 L working volume fed batch fermenter run every two weeks for a year. Extrapolating, the C-flow system yields 3 kg of test protein per year at 1 g/L, or 18 kg/yr at 6 gm/L. This is consistent with the observation made above that on a one-off basis C-flow will be about 20 times more productive than fed batch with each run for the same elapsed time.

The degree of cost-efficiency improvement is much greater in proportion to degree to which fermentation can be extended, which in turn is directly correlated to low mutation rate of the host cell and the use of a two chamber fermenter design which reduces selection for mutations.

Even at the 1 L working volume scales used in the Examples provided herein, the C-flow system is observed to produce much higher levels of protein product than even 10 L scale batch fermentations are capable of producing on the same time scale.

Projections of the cost efficiencies of C-flow vs. fed batch are shown in the table below;

| C-flow | | | | | | | | |
|---|---|---|---|---|---|---|---|---|
| | 1 L vol 0.05 L/hr | | 1 L vol 0.1 L/hr | | 1 L vol 0.25 L/hr | | 1 L vol 0.5 L/hr | |
| weeks | g CRM | cost/g | g CRM | cost/g | g CRM | cost/g | g CRM | cost/g |
| 2 | 8 | 897 | 17 | 469 | 42 | 211 | 84 | 126 |
| 4 | 25 | 408 | 50 | 217 | 126 | 103 | 252 | 65 |
| 6 | 42 | 310 | 84 | 167 | 210 | 81 | 420 | 53 |
| 52 | 428 | 177 | 857 | 99 | 2142 | 52 | 4284 | 36 |

| Fed batch | | | | | | |
|---|---|---|---|---|---|---|
| | 5 L | | | 100 L | | |
| weeks | g CRM | run cost | cost/g | g CRM | run cost | cost/g |
| 2 | 10 | 12200 | 1220 | 100 | 32000 | 320 |
| 4 | 20 | 24000 | 1220 | 200 | 64000 | 320 |
| 6 | 30 | 36000 | 1220 | 300 | 96000 | 320 |
| 52 | 260 | 312000 | 1220 | 2600 | 832000 | 320 |

Cost efficiency calculations for the fed batch continuous production are approximated by assuming 5 L fed batch fermentations can be repeated weekly and 100 L fermentations biweekly. Each fermentation volume was evaluated at a fixed price per fermentation. C-flow was modeled as a 1 L volume using the two flow rates that have been demonstrated experimentally; 5 L continuous flow rates were scaled proportionately. C-flow costs assume a week for setup and only minor maintenance efforts after that.

The table above shows that the projected cost per gram of test protein drops as the time of C-flow fermentation increases, because running costs are much lower than the startup costs. Much of this benefit of C-flow is realized by four to six weeks of extended fermentation and the advantages are significant even at two weeks, which are in the range of typical production campaigns. All four rates of C-flow production show this benefit at four to six weeks. Experimental results indicate that this level can be reached by the current C-flow configuration described here. More surprising is the prediction that the 5 L C-flow at flow rate of 0.5 L/hr could outperform a 100 L fermenter by producing 30% more product at ⅙ the cost per gram of test protein in the same time period. This same C-flow system could produce the same output in one year as a 4200 L fed batch fermenter.

A person skilled in the art would understand that C-flow systems can produce significantly higher quantities of biological products than traditional batch or fed batch fermentation systems and that the physical footprint of a C-flow system is significantly smaller than the equivalent traditional fermentation systems. The current application contemplates production of C-flow systems as a single integrated unit suitable for use with containment hoods or other confined spaces within existing fermentation suites or even in portable or mobile applications. Such integrated C-flow systems may comprise inlet and outlet plumbing as well as electronic access to monitoring sensors so that it can be coupled to specific media reservoirs, inoculated with the desired production organism and attached to sensor monitors and downstream processing systems in a manner conducive to operating the fermentation as a single disposable integrated device that may be discarded at the end of the production run.

A. Multi Gravimetric Systems

A number of unique modifications to standard fermentation equipment are also contemplated to allow use of multi gravimetric feed inputs.

Figure 3:
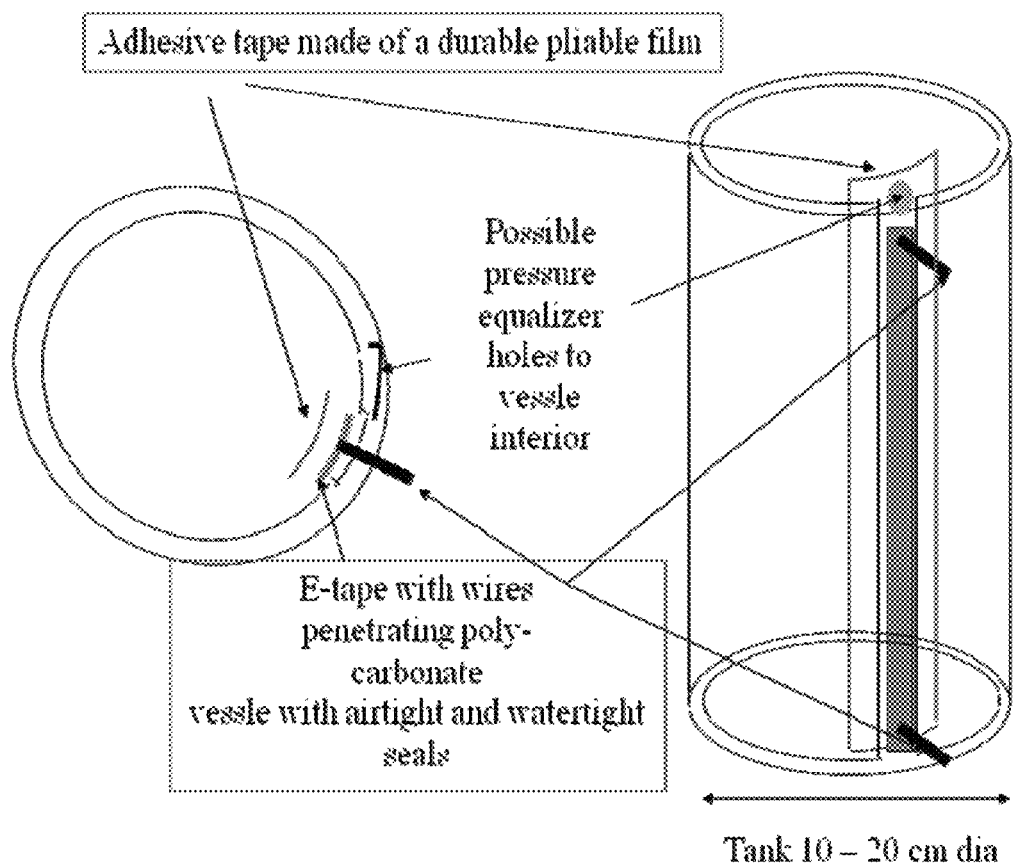
FIG. 3 is a diagram of the E-tape sensor for continuous monitoring or control of culture level.

One such modification, called an E-tape sensor, provides for continuous monitoring of the culture level within the modified fermentation vessels. The apparatus itself comprises an adhesive backed durable pliable film comprising conductive wires and optionally equipped with holes spaced along the longitudinal axis of the pliable film suitable for allowing pressure equalization across the film. The wires are arranged to match ports within the vessel wall and are connected to external conductivity sensors via airtight and watertight seals, for example as shown in FIG. 3.

Figure 4A:
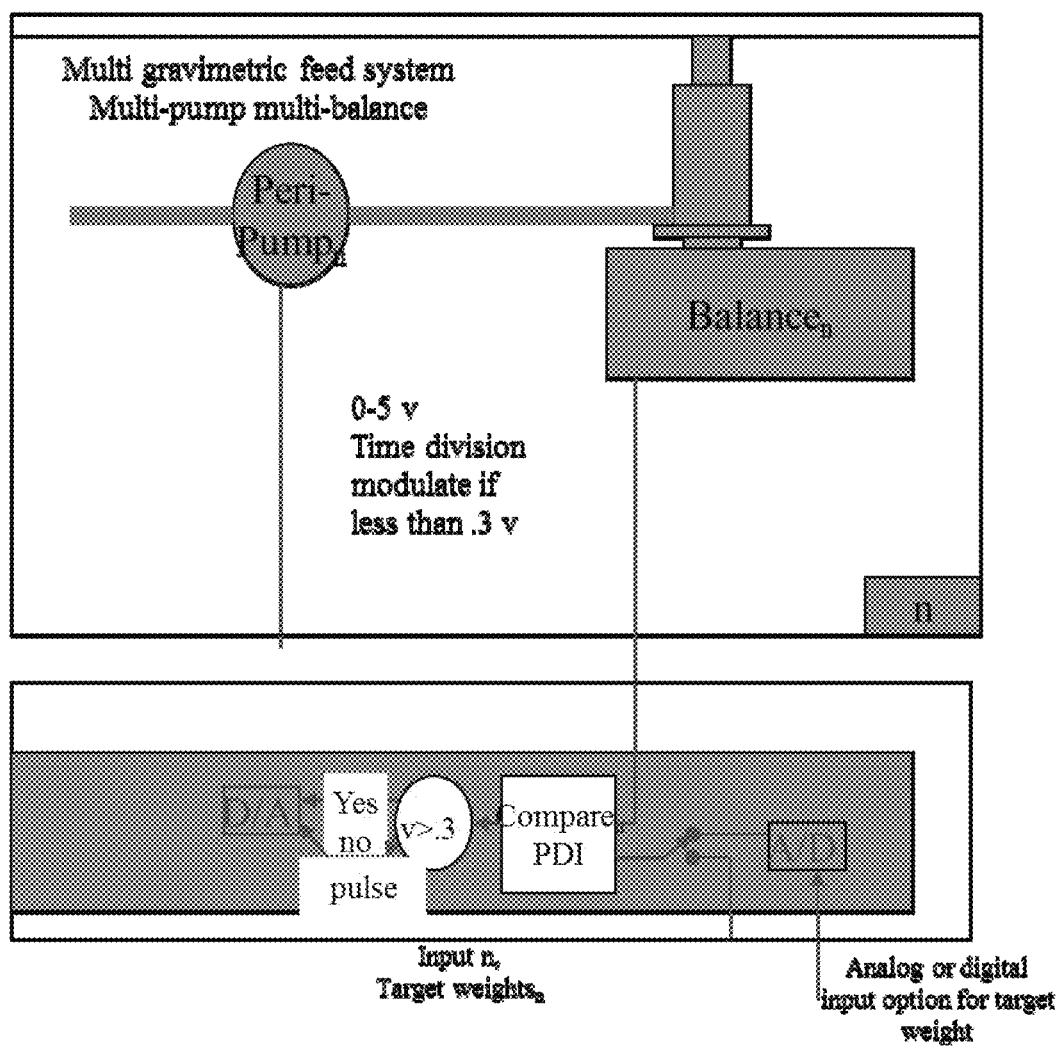
FIG. 4a depicts a multi gravimetric feed system using a multi pump, multi balance configuration.
Figure 4B:
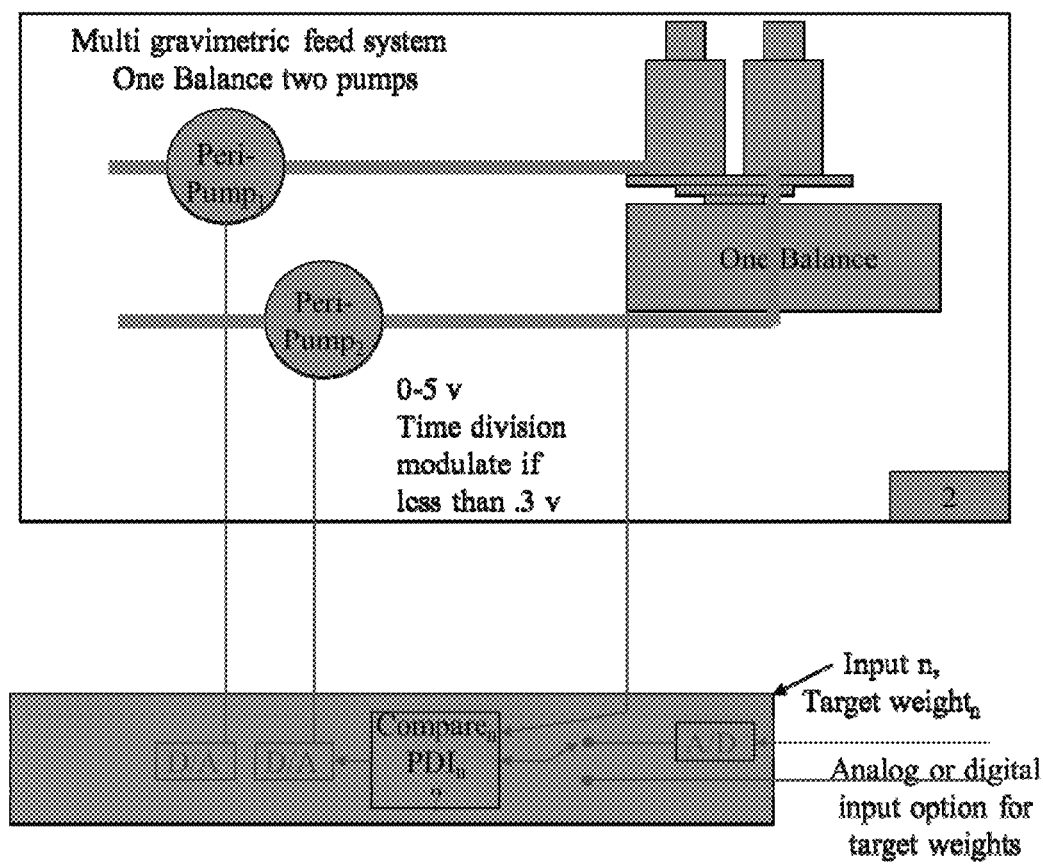
FIG. 4b depicts a multi gravimetric feed system with a one balance two pump system.
Figure 4C:
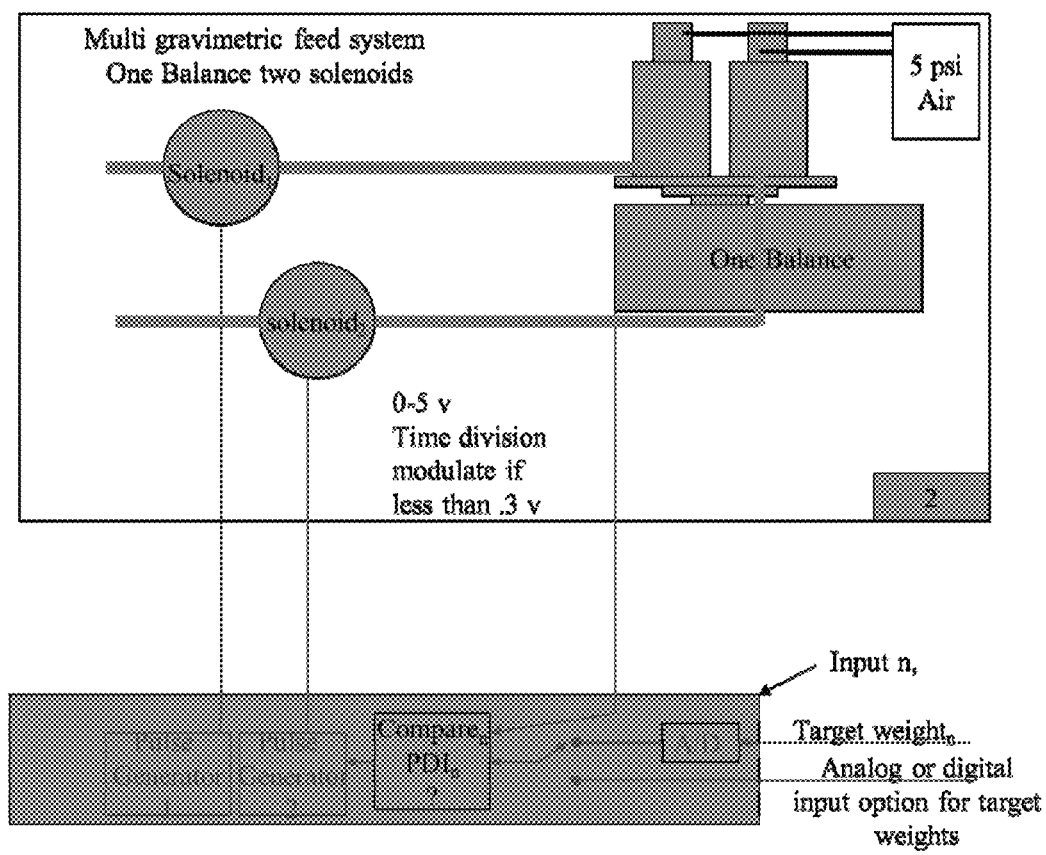
FIG. 4c depicts a multi gravimetric feed system with a one balance two solenoid configuration.

Another modification comprises a system for multiple feed inputs to allow separate feed components to be added in various combinations and ratios. Such a system is useful not only to facilitate design of experiment (DOE) operations, but once the desired operational parameters have been determined, to allow high concentration feedstocks to be used without danger of precipitation, discoloration or other chemical or physical cross-reactions between feed stock components. One common example of such cross reactions is the interaction of phosphate with certain metals present in trace element stocks, such as calcium or magnesium, resulting in precipitation of calcium phosphate or magnesium phosphate crystals. Multiple configurations of such methods are possible. FIG. 4a depicts a multi gravimetric feed system using a multi pump, multi balance configuration. FIG. 4b depicts a multi gravimetric feed system with a one balance two pump system. FIG. 4c depicts a multi gravimetric feed system with a one balance two solenoid configuration.

Figure 5:
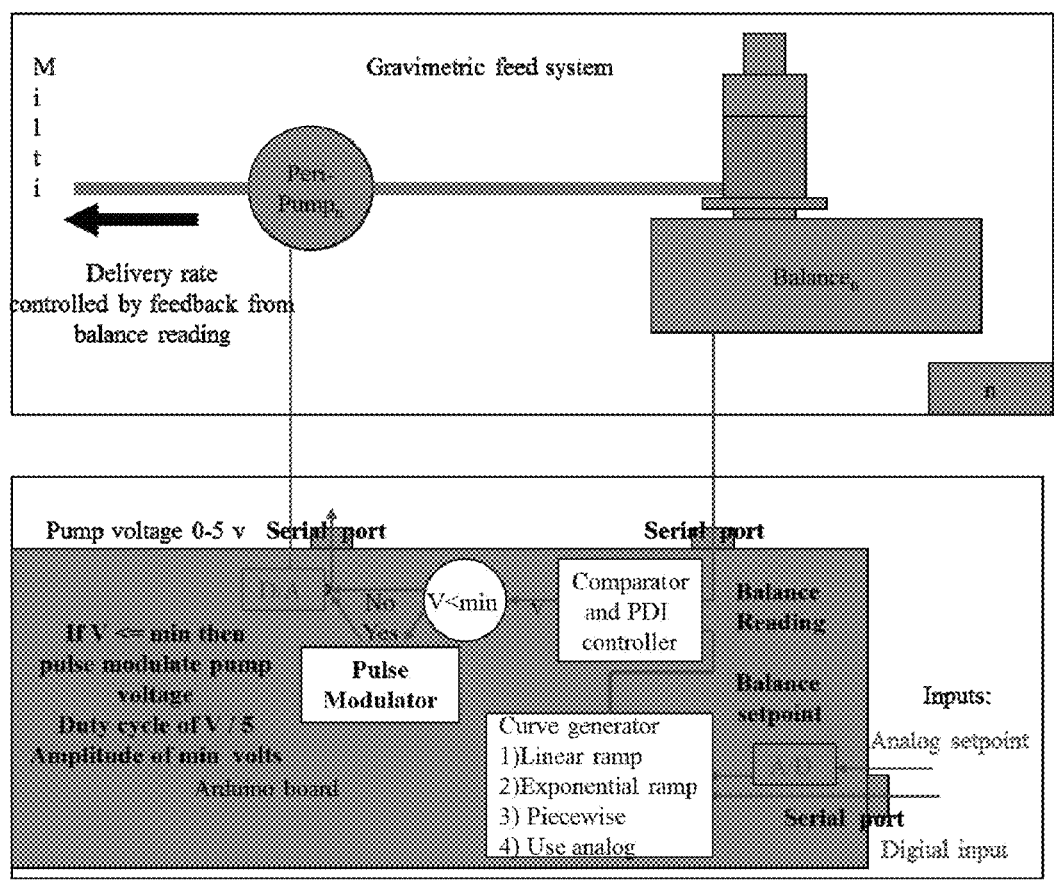
FIG. 5 represents how the multi gravimetric systems depicted in FIGS. 4a-c are integrated into the overall control scheme.

In the overall control scheme shown in FIG. 5, the peristaltic pump delivers volume at a rate proportional to the control voltage (0 to 5v) depending on the tubing diameter. The calibration is not particularly linear with pump rate and is not stable due to variations in viscosity and the pressure being pumped against and other random factors. Over time the tubing also deforms, wears out, changes the time constant of elasticity, and is variable with temperature. To account for such non-linear and unpredictable variations feedback control from a bottle on a digital balance allows long term stability and accuracy of the pump rate.

In the fermentation application the feed of nutrients may be specified to follow a defined program such as an exponential, linear or step function. Pumping can be somewhat intermittent as long as the programmed curve is followed with accuracy on the 1 to 5 minute timescale. This makes gravimetric control with a feedback loop a good design choice.

Often the feed curve of the fermentation covers a wide range of pumping rates including very slow rates. Peristaltic pumps are problematic at low pump rates. Below a certain voltage they stall. Pulse width modulation of the pump speed signal between zero and the minimum voltage necessary to provide some delivery is the best solution when a low pump rate is called for.

Fermentation often calls for multiple substances to be pumped. One reason for multiple pumps is to avoid precipitation in stock solutions. For example, magnesium, phosphate and sugar solutions may be fed slowly from separate bottles at the same rate as the cells are taking them up so they don't accumulate in the culture media. A second reason is to control for accidental variations such as evaporation or pH changes.

Since digital balances and peristaltic pumps are expensive, it can be worthwhile to multiplex. Using one balance to control several pumps is the reasonable first step. Using the same pump for multiple feeds is feasible but requires care to avoid mixing of incompatible substances. Under gravimetric control a cheap pump with poor stability or even a pulse delivery pump can perform well as far as overall stability in a fermenter feed application is concerned.

Examples may be solenoid valves in a system pressurized with air or spring loaded piston pump bottles similar to the kind that liquid detergents are sold in. These can also be actuated directly with a solenoid.

Figure 6:
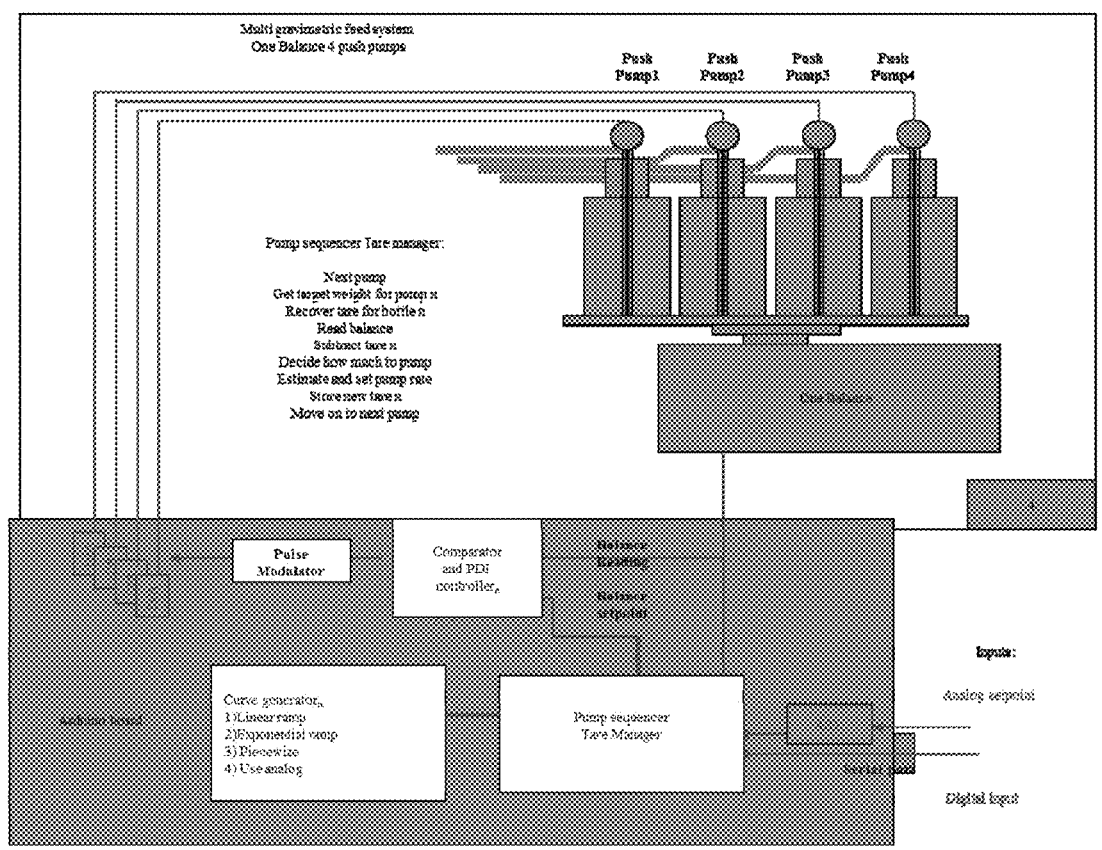
FIG. 6 depicts a multi gravimetric feed system comprising one balance and four push pumps.

To reliably configure multi gravimetric systems efficiently a standard protocol incorporating some or all of the following steps is required. The steps depicted here are those determined necessary to properly configure a one balance four push pump configuration as shown in FIG. 6. Step 1 requires setting the tare manger program, step 2 requires determining the target weight for pump n, step 3 recover tare for bottle n, step 4 read the balance, step 5 subtract tare n, step 6 determine how much to pump, step 7 estimate and set the pump rate, step 8 store the new tare n, and then move onto the next pump and repeat the process.

B. Sparger Modifications

Figure 7:
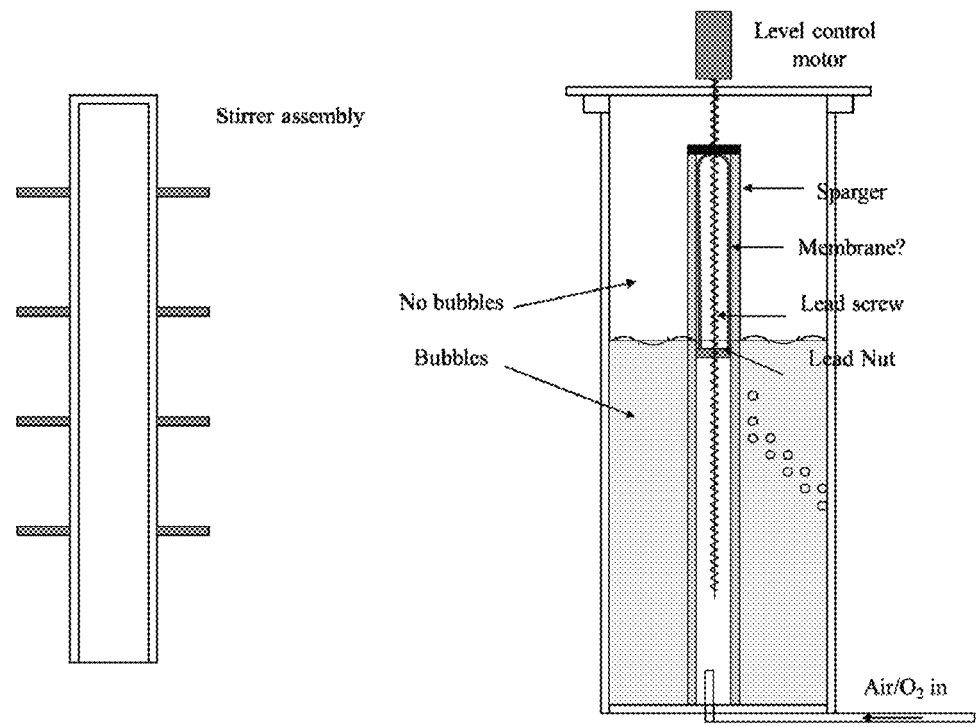
FIG. 7 is a diagram of the sheathing system allowing variable sparger adjustment within the fermentation vessel.

Efficient gas, usually oxygen, delivery to the fermentation vessels requires delivering gas only to the culture liquid in a form that maximizes availability to the cells in the vessel. FIG. 7 depicts a sheath system for minimizing distribution of sparged gases to the headspace of the fermentation vessel allow a single sparge unit to be efficiently used in a single fermenter with variable working volumes. The system comprises a gas impermeable membrane affixed to a metal jacket that closely engages the outer surface of the sparging element. The device is raised or lowered as culture volume is increased or decreased, respectively, in order to seal the sparger above the culture level and prevent discharge of gas into the headspace, as shown in FIG. 7.

Figure 8:
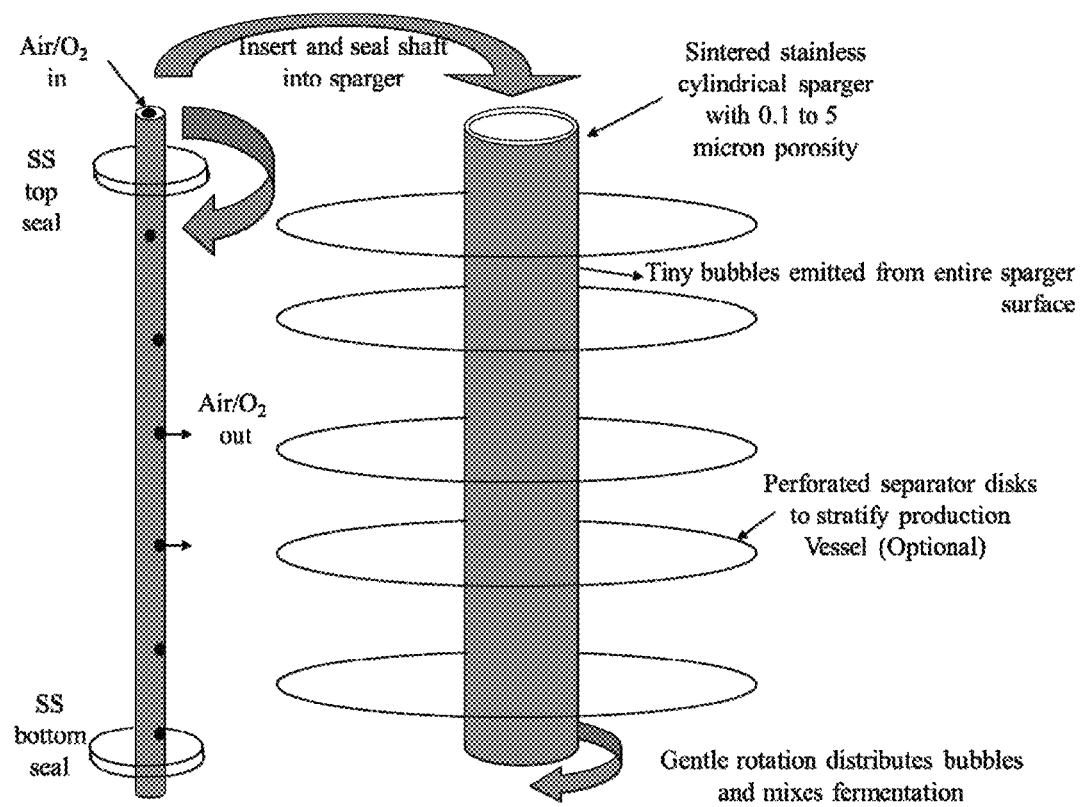
FIG. 8 is a diagram of a sparging device comprising an outer sheath fitted with planar disk elements to retain dissolved gases and small bubbles within the culture media.

To further improve gas distribution within the fermentation vessel the sparger, with or without the sheath system, is configured to fit within a metal shaft upon which a plurality of flat disks with outer diameters less than the maximum interior diameter of the fermentation vessel are affixed. The top and bottom of the metal shaft are sealed so that the pressurized gas can only diffuse through small pores, preferably 1 to 5 micron porosity, where upon they are segregated between the flat disks, which serve as a baffle system to retard escape of gas bubbles into the headspace. Such a system is depicted in FIG. 8.

EXAMPLES

Example 1

Figure 9:
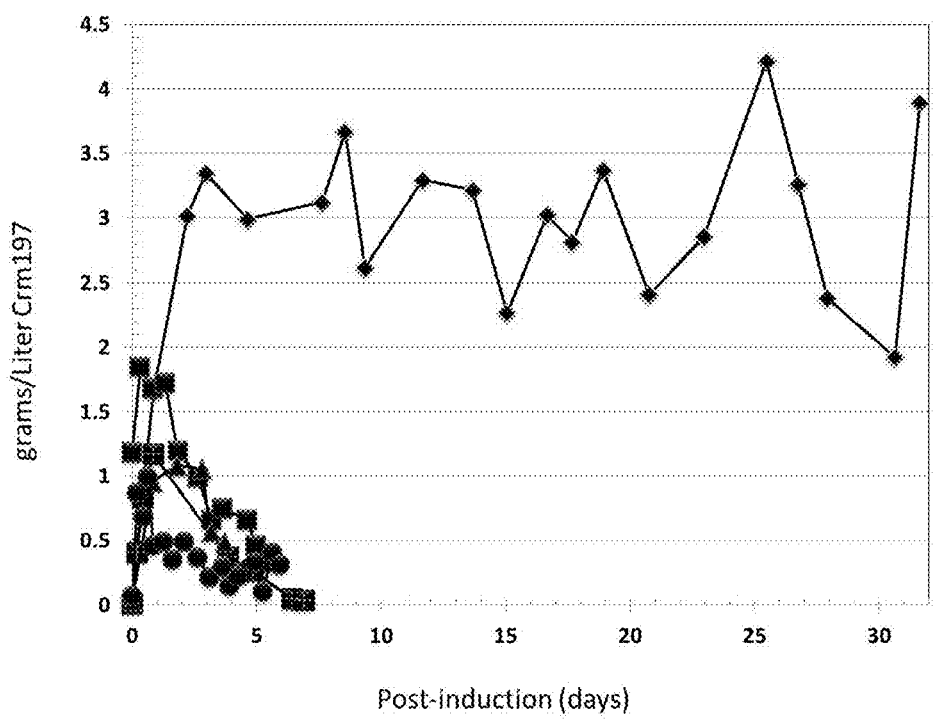
FIG. 9 is a plot of the amount of Crm197 test protein produced each day by MDS69 meta ΔrecA (diamonds), BL21/DE3 (squares), MG1655 ΔrecA (triangles) and BLR (DE3) (circles), each containing the pSX2-Crm197 expression vector and grown in the C-flow fermenter as described.

Reduced Genome Bacterial Strains are More Stable in Continuous Fermentation Than Unreduced Bacterial Strains and Produce Greater Product Yield Over the Course of Fermentation To test the ability of a reduced genome bacterial strain to produce proteins in extended C-flow fermentation, a periplasmic test protein (CRM197) was measured. The C-flow experiments employed the low mutation strain *E. coli* MDS69 meta ΔrecA (engineered to be genetically stable and metabolically efficient in fermentation) or commonly used *E. coli* production strains, including BL21/DE3, BLR and MG1655 ΔrecA. Comparison of yield profiles of each of these strains, shown in FIG. 9, indicates reduced genome strains significantly improve protein production relative to commonly used production strains in C-flow fermentations.

In these experiments all strains were transformed with the same Crm197 expression plasmid construct based on plasmid pSX-2 T5lacO with kanamycin as the selectable marker (described in International Publication No. WO/2015/134402 herein incorporated in its entirety; commercially available from Scarab Genomics LLC, Madison, Wis.). All strains were tested in the C-flow system configured as shown in FIG. 1. Following chemostat stabilization in seed and production vessels at an OD of about 200 and temperature stabilized to 25 C, the culture in the production vessel was induced with 100 μM IPTG. Test protein was identified in total cell homogenate samples within hours of induction and was then found to increase over the next few days. Within one to three days after the start of induction test protein levels reached peak values, similar to or exceeding yields obtained in fed-batch fermentations. Strikingly, the commonly used production strains only produced peak levels of test protein for a short period of time and productivity began to degrade rapidly thereafter. Within a few days of initiating continuous culture the productivity of these strains had degraded to less than 0.5 g/L of product and in some cases the culture collapsed (lysed or washed out) completely. In contrast, the reduced genome bacterial strains continued to make high levels of product for more than 4 weeks with the cell density remaining high throughout the course of the fermentation.

In the relatively small scale C-flow system described here (working fermentation volume of about 1 L at a flow rate of 0.25 L/hr) the reduced genome bacterial strain produced about 100 g of CRM197 over the course of a month. The typical *E. coli* strains (BL21/DE3, BLR and MG1655 ΔrecA) produced less than 5 g of Crm197 over the course of their respective fermentations, none of which lasted more than a week before culture collapse. In addition to producing lower overall peak levels of test protein, the unmodified *E. coli* strains were only capable of sustaining peak levels of production for a few days, whereas the reduced genome expression strain sustained peak expression throughout the entire of the extended fermentations of more than a month. The reasons for collapse remain uncertain, but in some cases appears to be due to cell lysis, the result of induction of endogenous prophage or other lytic elements, in other cases sequence analysis of the fermentate indicates the cultures were contaminated with other microbes and the observed culture collapse may be due to toxins or other compounds produced by such contaminants. Importantly, the reduced genome bacterial fermentations were not subject to culture collapse, indicating that the enhanced genetic stability of such strains minimized the chance of any induction of lytic elements from the strain itself. In addition, the lack of any deleterious effects on the reduced genome bacteria from contaminants suggests that the continuous introduction of un-contaminated reduced genome bacteria from the seed vessel into the production vessel minimizes the ability of contaminants to dominate the production vessel.

The C-flow fermentation systems comprising the hardware modifications described here and containing reduced genome bacterial strains with enhanced genetic stability and improved metabolic capacity are capable of producing at least 20 times more product than typical strains of E. coli currently used in fermentation. The combination of improvements such as the gravimetric feed configuration and sparger modifications described herein and the reduced genome bacterial strains allow extended C-flow fermentations to produce large amounts of product from relatively small amounts of fermentate. The hardware system improvements described here allow more robust control of fermentation parameters and enhance the reliability of the mechanical systems, while the improved genetic stability of the fermentation organism improves the longevity of the culture and minimize the risk of culture collapse due to induction of endogenous prophage, genetic rearrangement or exogenous contamination. This unique combination of hardware modifications and strain modifications result in a highly productive stable platform for making proteins and other fermentation products at high levels relative to current strains and methods.

Example 2

Reduced Genome Bacterial Strains in Continuous Fermentation Produce Greater Product Yields for Many Different Proteins To determine whether the benefits of using reduced genome bacteria in the C flow fermentation system are unique to producing the Crm197 test protein two additional test proteins were examined. Recombinant EPA (rEPA) is a recombinant variant of exoprotein A from *Pseudomonas aeruginosa* frequently used as a carrier protein for conjugate vaccines. As with Crm197, the rEPA protein is difficult to produce in *E. colii*, with typical yields of about 0.1 g/L in optimized batch fermentations. Another protein, human gelsolin was also tested. Gelsolin is typically produced at less than 2 g/L by typical *E. coli* production strains grown in optimized batch fermentations.

Figure 10:
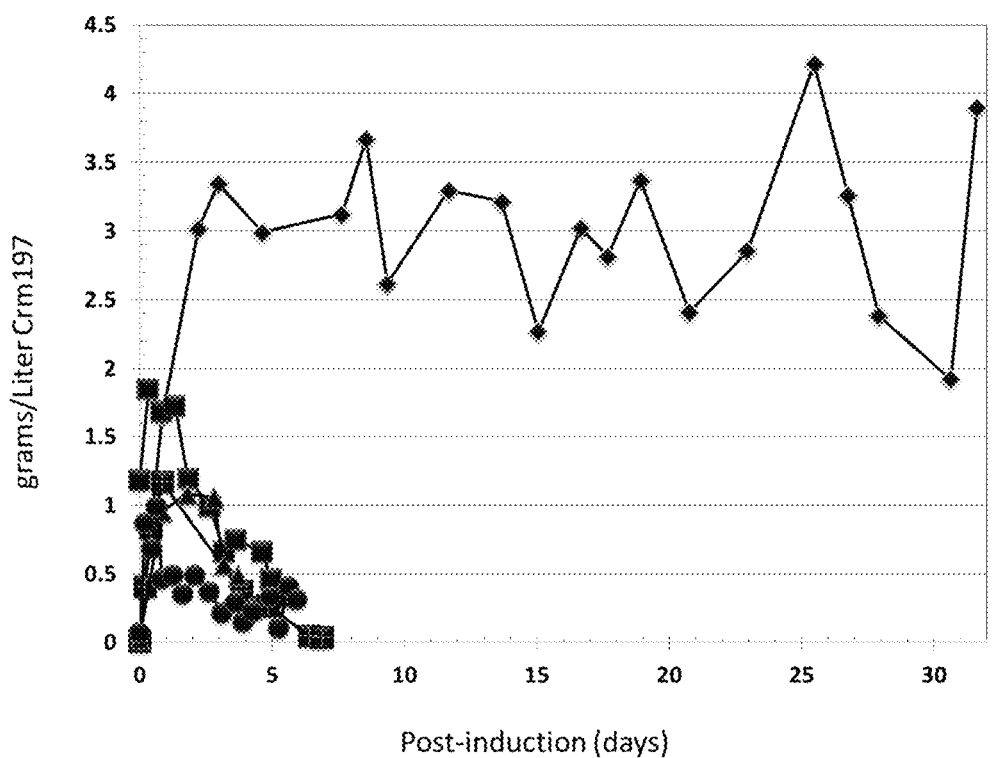
FIG. 10 is a plot of the amount of rEPA test protein produced each day by MD69 meta ΔrecA containing the pSX2-rEPA expression vector and grown in the C-flow fermenter as described.

The gene encoding rEPA was cloned into the pSX-2 T5lacO plasmid expression system and transformed into MDS69 meta ΔrecA using standard microbial methods. The transformed cells were inoculated into the dual tank 1 L working volume C-flow system and the fermentation was conducted as described in Example 1. As shown in FIG. 10 the induced cells produced approximately 2 g/L of rEPA for a period of 20 days resulting in a total measured yield of about 25 g. In comparison, 4 successive 10 L working volume batch fermentations will produce about 3 g of rEPA in the same period of time (assuming a 5 day turnaround schedule per fermentation within the same 20 day period).

Figure 11:
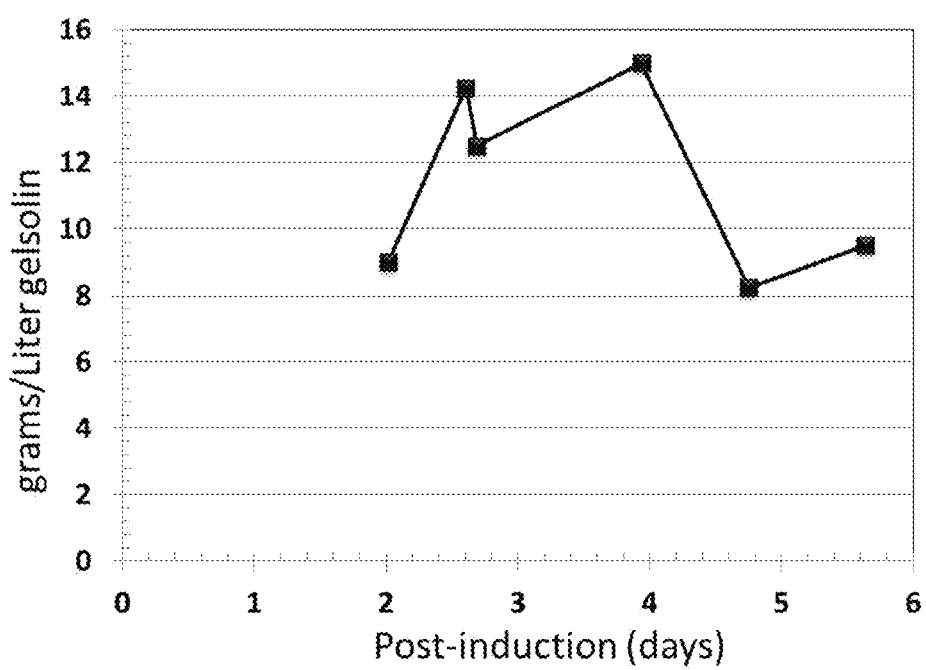
FIG. 11 is a plot of the amount of human gelsolin test protein produced each day by MD69 meta ΔrecA containing the pSX2-gelsolin expression vector and grown in the C-flow fermenter as described.

The gene encoding codon optimized human gelsolin was cloned into the pSX-2 T5lacO plasmid expression system and transformed into MDS69 meta ΔrecA using standard microbial methods. The transformed cells were inoculated into the dual tank 1 L working volume C-flow system and the fermentation was conducted as described in Example 1. As shown in FIG. 11 the induced cells produced approximately 10-14 g/L of gelsolin over a period of 6 days resulting in a total measured yield of 27 g. In this case the C-flow apparatus was prematurely terminated by an unscheduled software update from Microsoft. By way of comparison, a 10 L working volume batch fermentation typically produces less than 18 g of gelsolin on a similar time scale (assuming a 5 day turnaround per fermentation within the same time period).

In all cases tested the reduced genome bacteria grown in the C-flow system produced significantly higher levels of test protein than observed from typical strains grown in optimized batch fermentations, indicating that the combination of reduced genome bacteria and C-flow fermentation provides a production platform capable of generating relatively high levels of valuable protein products over extended periods at lower cost and with higher efficiency than traditional fermentation strains and methods.

I claim:

1. A continuous fermentation process for the production of a biological product comprising culturing a population of reduced genome *Escherichia coli* (*E. coli*) bacteria cells comprising an inducible expression vector encoding a biological product in at least two successive fermentors, each configured as an independent continuous flow chemostat, said fermentors comprising a first fermentor comprising culture medium wherein said cells are cultured under uninduced conditions and a second successive continuous fermentor for producing the biological product comprising culture medium comprising inducer and further comprising an amount of said culture medium from said first fermentor sufficient to inoculate said second fermentor, wherein said cells are cultured under suitable conditions to produce the biological product for a period of at least two weeks, and wherein the biological product is recovered from said second fermentor, wherein the reduced genome *E. coli* are genetically engineered to lack transposable genetic elements.

2. The method of claim 1, wherein each fermentor is fed glucose minimal salts medium using a dual feed approach that separates delivery of phosphate from other media components.

3. The method of claim 1, wherein the reduced genome bacteria cells are MDS69 meta ΔrecA cells.

4. The method of claim 1, wherein said culture medium in said fermentors are gravimetrically fed.

5. The method of claim 4, wherein gravimetric feed is accomplished by a multigravimetric system comprising a plurality of pumps and a plurality of balances to regulate flow through the fermentors.

6. The method of claim 1, wherein the biological product is a protein.

7. The method of claim 6, wherein the protein is Crm197, rEPA or gelsolin.

8. The method of claim 1, wherein the *E. coli* cultures in each of the successive fermentors is stabilized at an optical density at 600 nm (OD600) of at least about 200.

* * * * *